United States Patent [19]

Siepser

[11] Patent Number: 4,976,719

[45] Date of Patent: Dec. 11, 1990

[54] DEVICE USED TO CHANGE CORNEAL CURVATURE

[76] Inventor: Steven B. Siepser, 866 Downingtown Pike, West Chester, Pa. 19380

[21] Appl. No.: 273,992

[22] Filed: Nov. 21, 1988

[51] Int. Cl.$^5$ ............................................. A61B 17/12
[52] U.S. Cl. ................................... 606/151; 606/201; 24/277
[58] Field of Search ............. 128/303 R, 330, 92 YD, 128/346; 24/277, 283, 20 LS; 606/152, 153, 155, 156, 166, 201, 221, 1, 151

[56] References Cited

U.S. PATENT DOCUMENTS

| | | | |
|---|---|---|---|
| 2,881,762 | 4/1959 | Lowrie | 606/157 X |
| 3,570,497 | 3/1971 | Lemole | 24/16 X |
| 4,671,276 | 6/1987 | Reynolds | 128/330 X |

FOREIGN PATENT DOCUMENTS

| | | | |
|---|---|---|---|
| 2354752 | 1/1978 | France | 128/303 R |
| 2141629 | 1/1985 | United Kingdom | 128/303 R |

Primary Examiner—Michael H. Thaler
Attorney, Agent, or Firm—Eugene E. Renz, Jr.

[57] ABSTRACT

This invention relates to a method for reducing all of the common refractive errors, myopia, hyperopia, and astigmatism in a reversible fashion and to a device for achieving same. More particularly, this invention relates to a method for reducing or eliminating nearsightedness by flattening the curvature of the cornea and to a method for reducing or eliminating corneal astigmatism by changing the out-of-round shape of the cornea to a round shape. All of the methods utilize a retainer ring permanently placed in the stroma of the cornea, the tensioning of the ring being controlled by a turnbuckle arrangement.

3 Claims, 1 Drawing Sheet

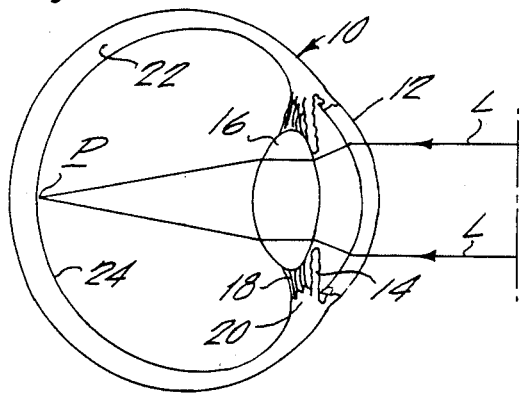
Fig. 1. (NORMAL)
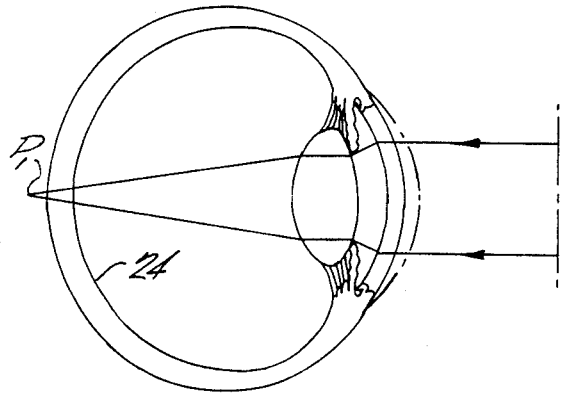
Fig. 2. (FAR SIGHTED)
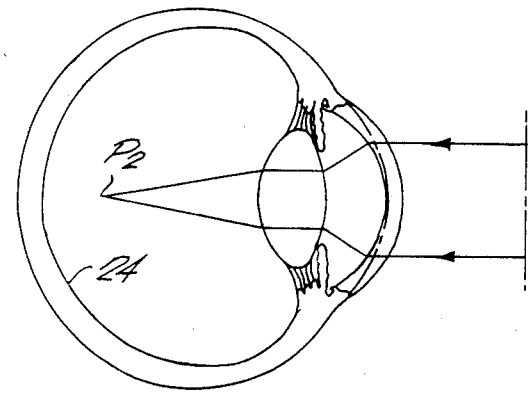
Fig. 3. (NEAR SIGHTED)
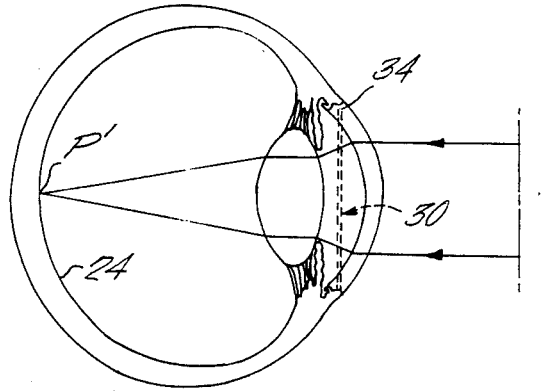
Fig. 4. (CORNEA-CORRECTED)
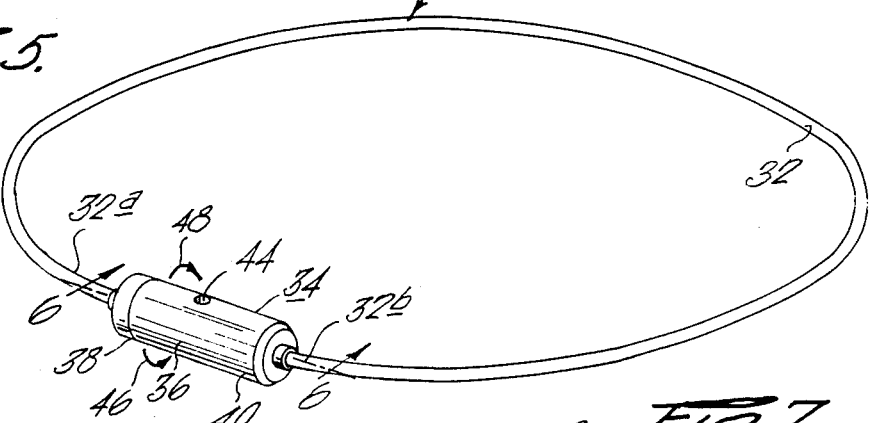
Fig. 5.
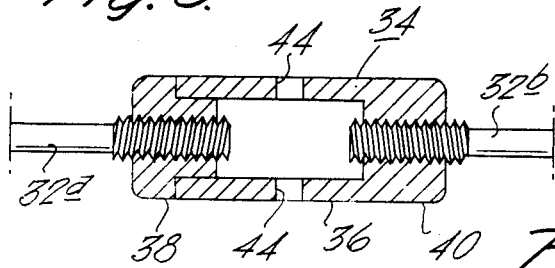
Fig. 6.
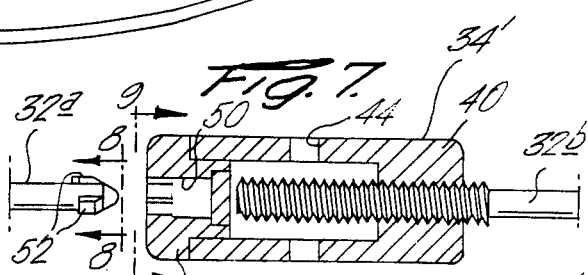
Fig. 7.
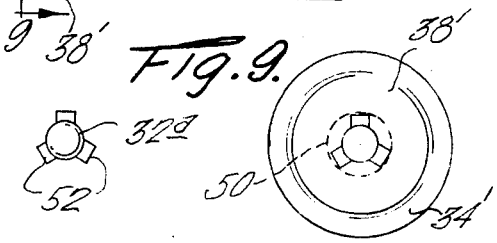
Fig. 8. Fig. 9.

DEVICE USED TO CHANGE CORNEAL CURVATURE

FIELD OF THE INVENTION

This invention relates to a method for reducing all of the common refractive errors, myopia, hyperopia, and astigmatism in a reversible fashion and to a device for achieving same. More particularly, this invention relates to a method for reducing or eliminating nearsightedness by flattening the curvature of the cornea and to a method for reducing or eliminating corneal astigmatism by changing the out-of-round shape of the cornea to a round shape. All of the methods utilize a retainer ring permanently placed in the stroma of the cornea, the tensioning of the ring being controlled by a turnbuckle arrangement.

BACKGROUND OF THE INVENTION

The eye is an organ that focuses incoming light waves onto sensitive nerves. These nerves transmit this information to certain parts of the brain, which in turn interprets them to give the sensation of sight. The act of "seeing" is truly a complex process. Basically, light waves coming into the eye must be bent, i.e. refracted in such a way that they come to a point that focuses on the nerves (retina) at the back of the eye. The two main tissues that bend incoming light are the cornea and the lens. Depending on the length of the eye, the cornea and lens may need to supply different amounts of focusing power. The total amount of power needed for the eye to focus light may be provided in different ratios. If the power of the cornea and the lens is not exactly correlated to the length of the eye, one is said to have a refractive error. The "big three" refractive errors are myopia, hyperopia and astigmatism.

Myopia (from the Greek "shut eyes", referring to the squinting of nearsighted people to see better for distance) is the most common refractive error. In the United States, about seventy million people have myopia and on a worldwide basis myopia affects about one quarter of the total population. Unaided by glasses or contacts, myopic or nearsighted people can see near but not far, since the nearsighted eye is naturally focused at close range. Myopia seems to be on the rise, though it is a mystery why. It is believed to be a result of heredity.

Another common refractive error is hyperopia, or farsightedness, which is the ability to see relatively better at a distance than close up. It occurs when the eye is too short. The lens and cornea are not powerful enough to converge light rays from close objects onto the retina. Even when looking into the distance, a farsighted person not wearing glasses must make a constant effort to focus.

A third refractive error is astigmatism. Astigmatism, from the Greek a, meaning "without", and stigma, meaning "point", results when the image is not focused to a point at all, usually because of an irregularly shaped cornea. When the cornea is so shaped, the rays of light from an object are bent irregularly and, thus, can't be sharply focused for either near or distance. Astigmatism may occur in an otherwise normal eye (simple astigmatism) or in a myopic or hyperopic one (compound astigmatism). Occasionally, the irregular curvature of the cornea may be such that in one direction, for example, vertical, the eye may be nearsighted and in the opposite, i.e. horizontal, axis, the eye may be farsighted. This is called mixed astigmatism.

The most common cause of astigmatism is a cornea that is oval in shape rather than round. A football standing on one end is an exaggerated example of an oval-shaped cornea. The flatter curve of the football from one tip to the other would refract or bend light less than would the steeper curve around the middle of the football. The two main curves of an oval refracting surface, such as an astigmatic cornea, are called meridians, and 90° usually separates the flattest from the steepest meridian. The degree to which the cornea is oval is microscopic.

For a person's vision to be clear without glasses or contact lenses, three structures in the eye have to work together almost perfectly: the cornea, the lens and the retina. The main function of the cornea and lens, as pointed out above, is to bend or refract light from objects so that the image comes to a pinpoint focus and falls on the fovea, the center of the macula. The macula is the critical part of the retina which gives a person sharp, clear vision. Whether light rays enter the eye parallel, as they do from distant objects, or non-parallel (divergent) as they do from near objects, it is up to the cornea and lens to correctly refract them so that the light rays focus precisely on the retina. If light is not brought to a point focus on the retina, vision will be imperfect because of the refractive error of the eye.

Refractive errors are measured in diopters, the unit of measurement of the refractive or light-bending power of the eye. Technically, one diopter is equal to the refractive power of a lens that has a focal length of one meter. A 2-diopter lens will focus parallel rays of light to a point one-half meter away, while a 4-diopter lens will bring light to a focus one-quarter meter (almost ten inches) away. The cornea has 40 diopters or two thirds of the eye's 60 diopters, while the refractive power of the lens is 20 diopters.

The major variables in the eye's exquisite and often imprecise refraction system are the length of the eye and corneal curvature. More accurately, it is the relationship or balance between the axial length, as the length of the eye is called, and the refractive power of the cornea and lens. In general mild to moderate refractive errors occur because of an imbalance between corneal curvature and axial length rather than a true abnormality. The more severe the refractive error, the longer (in myopia) or shorter (in hyperopia) is the length of the eye. Moreover, even if the length of the eye is "normal", a severe refractive error can still occur if the cornea is too steeply curved (in myopia) or too flat (in hyperopia). Normally, the distance from the front to the back of the eye is roughly 24 millimeters (almost an inch). When that distance, the axial length, is longer than normal and does not correlate with the refractive power of the lens and cornea, a refractive error results, i.e., myopia. Similarly, when the axial length is shorter than normal, hyperopia results.

If the eye is too long, light rays refracted or bent by the cornea and lens come to a focus in front of the retina and one is myopic (nearsighted). Similarly, if the cornea is curved too steeply for the length of the eye, a refractive error (hyperopia) will result. An understanding of the sensitive relationship between refractive power of the cornea and lens, and the length of the eye is important in understanding the present invention. The more curved the cornea, the more it will bend light rays and the further in front of the retina they will be focused.

The further this focal point lands in front or behind of the retina, the more severe the refractive error.

In summary, the fault in the myopic and the hyperopic eye is that the distance between the front and back of the eye is too long or too short compared to the curvature of the cornea. The fault in the astigmatic eye is that the cornea is irregularly curved, i.e., aspherical shaped, causing light rays to focus in two places. Both the eye distance and corneal curvature increase as people age, commonly causing increased levels of myopia. Glasses and contact lenses compensate for this disparity by altering the way light is bent as it enters the eye. Glasses and contact lenses do not cure refractive errors, i.e., myopia, hyperopia, and astigmatism. They only compensate for these conditions. To attempt to cure myopia, hyperopia, or astigmatism one must change either the length of the eye or the curvature or shape of the cornea. The device and method of the present invention take the latter route, namely, altering the curvature and/or shape of the cornea.

The general concept of making fixed changes in the corneal curvature of the eye is not new. A. E. Reynolds in the U.S. Pat. No. 4,452,235, for example, describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the end of the dissecting member, reversibly moving the dissecting member about the path pulling the adjusting member about the path, withdrawing the dissecting member, adjusting the ends of the split ring shaped adjusting member and fixedly attaching the end by gluing to maintain the desired topographical shape of the cornea.

To eliminate some of the complexity of the Reynolds procedure and to facilitate the adjustment of the diameter of the ring inserted in the stroma of the eye, Applicant has found the use of a turnbuckle arrangement most satisfactory. Such an arrangement is not only used to advantage in adjusting the ring size until the corneal topography approximates that of the indication of a desired topography but also to fixedly position the ends of the adjusting ring to the desired topographical shape of the cornea. The need for gluing is eliminated.

SUMMARY OF THE INVENTION

In order to reduce or eliminate myopia and hyperopia, as well as astigmatism, without resorting to radial keratotomy, keratophakia, keratomileusis, circling keratorraphy or laser keratorefractive surgery, it has been found that by flattening or steepening the curvature of the cornea or changing the shape of the cornea to spherical utilizing a biologically inert ring inserted in the stroma of the cornea with a turnbuckle for manually adjusting the diameter of the inserted ring, light beams entering the eye are focused properly on the retina and vision of distant or near objects is no longer blurry.

BRIEF DESCRIPTION OF THE DRAWINGS

The various features and details of the operation and construction of the present invention are hereinafter more fully set forth with reference to the accompanying drawings, wherein:

FIG. 1 shows schematically the focusing of a normal eye free of any refractive error.

FIG. 2 is similar to FIG. 1 but showing an abnormality of the cornea resulting in a condition known as farsighted or hyperopia.

FIG. 3 is similar to FIG. 1 but showing an abnormality of the cornea resulting in a nearsighted condition known as myopia.

The combination of FIGS. 2 and 3 disposed at right angles to one another would result in a condition known as astigmatism. Some rays are focused in the front and some are focused behind the retina due to incorrect curvature of the cornea in opposed planes and in more complex cases where the lens itself is abnormally curved.

FIG. 4 is a view similar to FIG. 1 showing an implant of this invention in position to return the cornea to a normal curvature resulting in proper focusing of light rays on the retina.

FIG. 5 is a greatly enlarged prospective view of the implant device of this invention utilizing the preferred embodiment of the adjusting means.

FIG. 6 is a side elevation illustrating in more detail the adjusting means shown in FIG. 5; and FIG. 7 shows a modified adjustment means, while FIG. 8 and FIG. 9 are sectional views taken along line 8—8 and 9—9 of FIG. 7, respectively.

DETAILED DESCRIPTION OF THE PREFERRED EMBODIMENT

The process of this invention is directed at correcting the three most common refractive disorders of the human eye, myopia, hyperopia, and astigmatism and involves changing the shape of the cornea, e.g., by flattening or steepening the curvature of the cornea, or by removing a bulge in it.

The cornea, the clear, dome-shaped tissue that covers the inner parts of the eye, acts as the "window" of the eye and is in part responsible for focusing the light rays; unlike the crystalline lens of the eye, the shape and focusing power of the cornea remain constant unless altered by external forces. The cornea is the most sensitive part of the eye, (it has the highest density of nerve endings per square millimeter) but reshaping the cornea does not harm it.

The lens in the human eye can only adjust so much in an effort to bring objects into focus. When the eye can't focus properly, there are certain basic conditions known as refractive errors that may be the cause, as has been pointed out above. One of these refractive errors, myopia, occurs when the eyeball is too long for the lens' focal capacity. The patient's cornea and lens focus the image of a distant object in front of the retina, so vision is blurry except when looking at nearby objects. Another refractive error, hyperopia, occurs when the eyeball is too short for the lens' focal capacity. A third refractive error, astigmatism, occurs when the cornea is not perfectly round but has a bulge in it.

In contrast to orthokeratology, a technique wherein contact lenses are carefully prescribed to intentionally change the curvature of the cornea, the present invention employs a ring-like device made of any of a variety of biologically inert materials including, but not limited to, fine surgical stainless steel wire, dental wire, carbon fiber, piano wire, nickel-titanium wire, spring steel, and high strength plastic filaments, e.g. nylon thread. For cosmetic reasons, the material used to alter the corneal curvature or the overall shape of the cornea may be darkened. The device is embedded in the stroma of the cornea to flatten or steepen the curvature of the cornea or to change its oval shape. The underlying principle is to create a ring of traction forces in the stroma layer of the cornea acting from its mid-periphery to its center. The device has a turnbuckle arrangement for manually adjusting the size of the ring. For myopia patients, the turnbuckle could be turned in a tightening direction and for a hyperopia patient in an opposite or loosening direction. While the diameter of the ring-like device may vary within a millimeter or so, a preferred diameter is 9 mm. The tip of the wire being inserted in the stroma is preferably tapered or pointed to permit easy and trauma-free entry. Damage to the Bowman's membrane is minimal.

When a ring-shaped plastic material is implanted into the stroma, it is usually inserted only after a circular path has been established throughout the stroma layer by means of a coiled, stiff surgical wire. In establishing this track, the wire is inserted into the cornea by penetrating the epithelium layer and Bowman's membrane and finally into the stroma. The wire is then pushed throughout the stroma until it makes a complete loop, i.e. 360° turn. Care is taken not to damage the Descemet's membrane or the endothelium during this circling procedure.

To determine just how much flattening or steepening or overall shape change is needed to correct the myopic, hyperopic, or astigmatic eye, the ophthalmologist may utilize a keratometer or ophthalmometer, i.e. an optical scanning device, which determines the exact "topography" of the cornea. A system of mirrors measures the horizontal and vertical meridians of the cornea. This determines the steepness or flatness of the cornea and its degree of corneal astigmatism, an important part of the overall refractive error picture, and instrumental in determining the extent of corneal curvature correction.

For patients with myopia, the curvature of the cornea is decreased, i.e. flattened, to the extent that light rays entering the eye are refracted by the flattened cornea and lens to focus precisely on the retina rather than to a point of focus in front of the retina. With patients with hyperopia, the curvature of the cornea is increased, i.e. steepened, to the extent that rays entering the eye are refracted by the steepened cornea and lens to focus precisely on the retina rather to a point of focus behind the retina. For patients with astigmatism, the egg-shaped cornea is changed to the shape of a round ball.

The use of a turnbuckle arrangement to manually control the tension on the circling ring inserted in the stroma is an essential feature of Applicant's invention. By turnbuckle arrangement is meant any coupling or tightening device consisting of an oblong piece internally threaded at both ends into which the threaded wire is screwed. Its parts are described hereinafter with respect to one embodiment. The turnbuckle can be connected at any convenient place in the ring-shaped loop of wire, and several may be used in a series if required.

Since the cornea normally tends to return to its former curvature and overall shape, the device of the present invention is kept in the eye indefinitely. This prevents the cornea from returning to its original curvature and is not harmful to the eye. The procedure of this invention is reversible in the sense that the circling ring of plastic or metal can, if necessary, be cut loose anytime postoperatively with the aid of surgical scissors or a laser beam. The original refractive error is then restored. This reversible feature of the present invention affords an added margin of safety but no need is envisioned for needing same.

The various embodiments of the invention are further illustrated by the following example.

The overall schematic view of the eyeball 10 comprising a first light transparent lens shape aperture cornea 12, a light sensitive aperture means or lens 14, a principal lens 16 centrally located and supported by muscular tissue (suspensory ligaments) 18 which are connected to ciliary recesses 20 which cooperate to define the curvature of the lens. The remainder of the eye comprises the sclera 22 having an interior surface upon which the light rays of the normal eye is focused and known as retina 24. The light rays are schematically shown and designated L and in a normal eye are brought to focus on retina 24 at a point P.

In FIG. 2, light rays are brought to a focus at a point beyond the retina designated $P_1$.

In FIG. 3, the light rays are brought to a plane of focus $P_2$ in front of the retina 24. In FIG. 4, the light rays are brought to a normal focus of $P_1$ on the retina 24 by means of corneal correcting device of this invention 30. The implant device 30 consists of a length of wire 32 having a diameter of approximately 0.009 inch, the wire having terminal threaded ends 32a and 32b engaged in a threaded manner to a fine adjusting means or turnbuckle 34. The turnbuckle 34 comprises a main body portion 36 whose central portion is apertured and having cylindrical end portions 38 and 40. Cylindrical ends 38 and 40 have centrally and axially aligned threads 42 which cooperate with threads on the ends 32a and 32b for attachment of the wire member 32.

In addition, body portion 36 has a hole 44 which allows a pin (not shown) to be inserted to rotate the turnbuckle 34 to tighten or loosen the loop 32, as shown by arrows 46 and 48 respectively.

The surgeon makes a puncture of the cornea adjacent to the inner face of the clear cornea and opaque sclera region wherein lies a gelatinous material into which a free end of a wire 32 is inserted, preferably at a point normally covered by the upper eye lid. The free end of the wire is carefully advanced and traces a circular path back to the origin of insertion. The surgeon then attaches one end of the wire to the turnbuckle fine adjustment assembly 34 as at 38. He then either manually expands or contracts the loop of wire embedded in the cornea until the light rays are brought into focus upon a target. He then removes an excess of the free end of the wire allowing just sufficient material to be attached to the fine adjustment means 34 as shown in FIG. 5 at 32b before attachment of the terminal end of this wire to the fine adjustment means 34. An incision of perhaps 4 to 5 mm. in length must be made extending from the point of wire insertion along the locus of the path that would be generated by a completed circle of the wire. Now the threaded free end 32b is coupled to the threadable end 40 by rotating body 34. The fine adjustment means is then actuated to bring the light rays back into the desired position on the target. When the surgeon determines that the cornea has been reshaped, that is, either making it more rounded through tension of the wire loop or expanding the diameter of the loop to create a flattening of the cornea, he then implants the device embedding it in the gelatinous material and sutured, if necessary.

In addition, in FIG. 7 there is shown a modification of a fine adjustment means such as 34 previously described. In FIG. 7 wire end 32a includes a different means for attaching the wire to the turnbuckle. A bayonet-type slot and key assembly 50, 52 as provided on wire 32a and end 38 so that the one end can be quickly attached and locked into position. Then, the same procedure as described above is used to attach end 32b to the turnbuckle. FIG. 8 shows an end view of key 52 on wire 32a. FIG. 9 shows the location of slot 50 in the adjustment means 34.

What is claimed is:

1. A device for changing the corneal curvature of nearsighted or farsighted persons comprising a length of surgical wire of small cross section for insertion into the stroma of the cornea of a human eye in a ring-like or circular channel in the stroma and adjustable means connecting opposite ends of said wire creating a ring of forces selectively adjustable to thereby permit selective change of the curvature of the cornea, said wire and said adjustable means generally lying on the annulus of the wire and adapted to be completely embedded in the cornea, the ends of said wire being threaded and the adjustable means comprising a turnbuckle having internal threads cooperatively associated with the ends of the wire.

2. A device as claimed in claim 1 wherein the wire is circular in cross section and a diameter of about 0.009 inches wire.

3. A device for changing the corneal curvature of nearsighted or farsighted persons comprising a length of surgical wire of small cross section for insertion into the stroma of the cornea of a human eye in a ring-like or circular channel in the stroma and adjustable means connecting opposite ends of said wire creating a ring of forces selectively adjustable to thereby permit selective change of the curvature of the cornea, said wire and said adjustable means generally lying on the annulus of the wire and adapted to be completely embedded in the cornea, one end of said wire being threaded and said adjustable means comprising a turnbuckle having internal threads cooperatively associated with said one end of the wire, the opposite end of said wire being provided with a key which selectively fits into a bayonet type slot in one axial end of the turnbuckle.

* * * * *